United States Patent
Kratz

(10) Patent No.: US 7,803,903 B2
(45) Date of Patent: Sep. 28, 2010

(54) PROTEIN-BINDING DOXORUBICIN PEPTIDE DERIVATIVES

(75) Inventor: Felix Kratz, Ihringen (DE)

(73) Assignee: KTB Tumorforschungs GmbH, Freiburg (DE)

( * ) Notice: Subject to any disclaimer, the term of this patent is extended or adjusted under 35 U.S.C. 154(b) by 0 days.

(21) Appl. No.: 10/548,185

(22) PCT Filed: Mar. 4, 2004

(86) PCT No.: PCT/EP2004/002204

§ 371 (c)(1),
(2), (4) Date: Sep. 7, 2005

(87) PCT Pub. No.: WO2004/078781

PCT Pub. Date: Sep. 16, 2004

(65) Prior Publication Data

US 2006/0173161 A1    Aug. 3, 2006

(30) Foreign Application Priority Data

Mar. 7, 2003  (DE)  ................................. 103 10 082

(51) Int. Cl.
*C07K 7/00*  (2006.01)
(52) U.S. Cl. ............ 530/328; 530/329; 530/345; 514/2; 514/152; 552/203
(58) Field of Classification Search ............ 530/328, 530/345; 514/152; 552/203
See application file for complete search history.

(56) References Cited

U.S. PATENT DOCUMENTS 6,844,318 B2 * 1/2005 Copeland et al. ............... 514/8
2002/0042375 A1 * 4/2002 Heimbrook et al. ........... 514/16

FOREIGN PATENT DOCUMENTS

DE  19926154  12/2000

OTHER PUBLICATIONS

Kratz et al. "Development and In Vitro Efficacy of Novel MMP2 and MMP9 specific Doxorubicin Albumin Conjugates", Aug. 6, 2001, Bioorganic and Medicinal Chemistry Letters, Oxford, GB, pp. 2001-2006.*
Mansour et al., "A New Approach for the Treatment of Malignant Melanoma: Enhanced Antitumor Efficacy of an Albumin-Binding Doxorubicin Prodrug That Is Cleaved By Matrix Metalloproteinase 2", Jul. 2003, Cancer Research, 63:4062-4066.*
Kratz et al., "Development and In Vitro Efficacy of Novel MMP2 and MMP9 Specific Doxorubicin Conjugates", 2001, Bioorganic & Medicinal Chemistry Letters, 11:2001-2006.*
Suzawa T. et al. "Enhanced Tumor Cell Selectivity of Adriamycin-Monoclonal Antibody Conjugate Via a Poly(Ethylene Glycol)-Based Cleavable Linker", 2002, Journal of Controlled Release, vol. 79. pp. 229-242.*
Newton (Expert Opinion on Investigational Drugs 9 (12) 2815 29, 2000).*
Formelli F (Cancer Chemotherapy and Pharmacology 21(4), 329-36, 1988).*
Wadler S (Cancer Research 48(3), 539-43, 1988.*
Matsunaga Seita (Cancer Chemotherapy and Pharmacology 58(3), 348-53, 2006).*
Villeneuve David J (Breast cancer research and treatment 96(1), 17-39, 2006).*
Cao Wei (Biochimica et Biophysica Acta 1763(2), 182-7, 2006).*
Munteanu Eliza (Biochemical Pharmacology 71(8), 1162-74, 2006).*
Flahaut Marjorie (Genes, Chromosomes & Cancer 45(5), 495-508, 2006).*
Kratz F et al: "Development and in virtro efficacy of novel MMP2 and MMP9 specific doxorubicin albumin conjugates" Aug. 6, 2001, Bioorganic & Medicinal Chemistry Letters, Oxford, GB, pp. 2001-2006, XP00208108.

* cited by examiner

*Primary Examiner*—David Lukton
(74) *Attorney, Agent, or Firm*—Millen, White, Zelano, Branigan, P.C.

(57) ABSTRACT

The invention relates to low-molecular doxorubicin peptide derivatives containing MMP-2 or MMP-9 divisible peptide sequences and a protein-binding group.

22 Claims, 5 Drawing Sheets

*significant compared to the control, +significant compared to doxorubicin

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Pro Gln Gly Ile Ala Gly Gln
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Gly Pro Leu Gly Ile Ala Gly Gln
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Pro Gln Gly Ile Trp Gly Gln
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Mal

<400> SEQUENCE: 4

Xaa Gly Pro Leu Gly Ile Ala Gly Gln
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Ala Gly Gln
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gly Ala Ile
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Leu Pro Gly
1
```

PROTEIN-BINDING DOXORUBICIN PEPTIDE DERIVATIVES

The invention concerns protein-binding doxorubicin-peptide derivatives which can be cleaved by the matrix metalloproteinases 2 and/or 9 and it also concerns their production and use.

The chemotherapeutic treatment of malignant diseases with doxorubicin is associated with side effects due to its narrow therapeutic range (Dorr R T, Von Hoff D D, "Cancer Chemotherapy Handbook" 2$^{nd}$ edition Appleton and Lange, Norwalk, 1994). Hence for a more effective treatment it is desirable to reduce the systemic toxicity of this cytostatic agent and at the same time to increase its pharmacological potential. It is known that certain prodrugs on the one hand, enable a targeted transport of bound active substances into the affected tissue and, on the other hand, result in an efficient release of the active substance at the target site which is as specific as possible as a result of biochemical or physiological characteristics of the malignant tissue. One approach to improving the side effect profile and the efficacy of cytostatic agents is the development of protein-binding formulations which couple in vivo to endogenous serum proteins and especially to albumin and in this manner represent macromolecular transport forms of the active substances (Kratz, F. et al., *J. Med. Chem.* 2000, 43, 1253-1256).

In addition matrix metalloproteinases (MMP), in particular MMP-2 and MMP-9, have been identified as important proteases for the progression of malignant tumors (Stetler-Stevenson, W. G. et al., *Annu. Rev. Cell Biol.* 1993, 9, 541-573).

In order to increase the therapeutic range of doxorubicin, the object of the invention is to create derivatives of this active substance which bind covalently to circulating albumin after intravenous administration and are cleaved by MMP-2 or MMP-9 in the tumor tissue. This object is achieved according to the invention by low-molecular doxorubicin-peptide derivatives of the general formula I

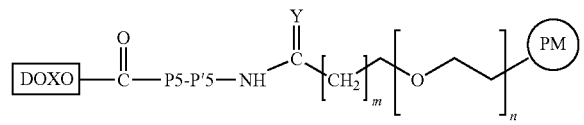

in which

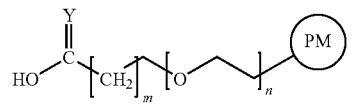 = doxorubicin (formula below)

Y=O or S
n=0 to 5
m=0 to 6

$P_5$-$P'_5$ denotes a peptide sequence consisting of up to ten of the 20 essential amino acids and PM is a protein-binding group.

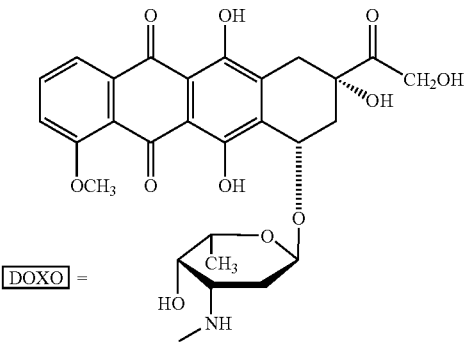

The compounds according to the invention are composed of doxorubicin, a peptide spacer and a heterobifunctional cross-linker containing a protein-binding group PM. This structure is elucidated in more detail in the following:

The heterobifunctional cross-linker is a carboxylic acid derivative having a protein-binding group of the general formula II in which
Y=O or S
n=0 to 5
m=0 to 6
PM=protein-binding group.

Heterobifunctional cross-linkers in which m<2 and n=2 to 5 are preferably used. The oxyethylene units ensure an increased water-solubility especially with relatively large values of n.

The protein-binding group (PM) is preferably selected from a 2-dithiopyridyl group, a halogen acetamide group, a halogen acetate group, a disulfide group, an acrylic acid ester group, a monoalkylmaleic acid ester group, a monoalkyl-maleaminic acid amide group, an N-hydroxysuccinimidyl ester group, an isothiocyanate group, an aziridine group or a maleinimide group. The maleinimide group is a particularly preferred protein-binding group.

The peptide spacer is a peptide sequence $P_5$-$P'_5$ consisting of up to ten of the 20 essential amino acids, which can be cleaved by MMP-2 and/or MMP-9. Preferred peptide spacers consist of eight amino acids. Particularly preferred sequences are

| peptide | |
|---|---|
| $P_5$ $P_4$ $P_3$ $P_2$ $P_1$ $P'_1$ $P'_2$ $P'_3$ $P'_4$ $P'_5$ | |
| Gly-Pro-Gln-Gly-Ile-Ala-Gly-Gln | (SEQ ID NO: 1) |
| Gly-Pro-Leu-Gly-Ile-Ala-Gly-Gln | (SEQ ID NO: 2) |
| Gly-Pro-Gln-Gly-Ile-Trp-Gly-Gln | (SEQ ID NO: 3) |

These peptides are enzymatically cleaved at the $P_1$-$P'_1$ bond by MMP-2 and/or MMP-9.

The sequence Gly-Pro-Leu-Gly-Ile-Ala-Gly-Gln (SEQ ID NO: 2) is most preferred.

The doxorubicin peptide derivatives according to the invention are expediently produced by reacting doxorubicin with a peptide derivative of the general formula III

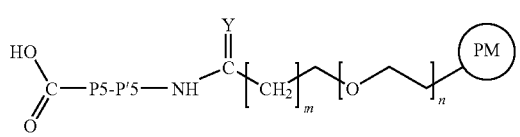

in which
Y=O or S
n=0 to 5
m=0 to 6

$P_5$-$P'_5$ denotes a peptide sequence consisting of up to ten of the 20 essential amino acids and PM denotes a protein-binding group, by condensing the activated carboxyl group of the peptide derivative with the amino group of the daunosamine ring of doxorubicin.

N,N'-dicyclohexylcarbodiimide, N,N'-diisopropylcarbodiimide, (benzotriazol-1-yloxy)-tris(dimethylamino)phosphonium hexafluorophosphate or 2-chloro-1-methyl-pyridinium iodide are preferably used as reagents to activate the C-terminal end of the peptide derivative with addition of common catalysts and/or auxiliary bases such as trialkylamines, pyridine, 4-dimethylamino pyridine (DMAP) or hydroxybenzo-triazole (HOBt). The reactions are expediently carried out in polar solvents such as DMF, DMA and/or DMSO at temperatures between −20° C. and 40° C., preferably at 0 to 5° C. and the reaction period is usually between 1 and 120 h, preferably between 24 and 96 h. The product can be isolated by standard methods such as crystallization, chromatography on silica gel or chromatography.

The peptide derivative is preferably prepared by reacting the activated carboxyl group of the heterobifunctional cross-linker of the general formula II with the N-terminal end of the peptide sequence $P_5$-$P'_5$. In this process N,N'-dicyclohexylcarbodiimide, N,N'-diisopropylcarbodiimide, (benzotriazol-1-yloxy)-tris(dimethyl-amino)phosphonium hexafluorophosphate or 2-chloro-1-methylpyridinium iodide are preferably used as reagents to activate the carboxyl group of the cross-linker with addition of common catalysts and/or auxiliary bases such as trialkylamines, pyridine, 4-dimethylaminopyridine (DMAP) or hydroxybenzotriazole (HOBt). The reaction is expediently carried out at the solid phase and the product is usually isolated by reversed phase chromatography (preparative HPLC) as is familiar to a person skilled in the art.

The protein-binding doxorubicin-peptide derivatives according to the invention are administered parenterally and preferably intravenously. For this purpose the doxorubicin-peptide derivatives according to the invention are provided as solutions, solids or lyophilisates, optionally using standard auxiliary agents such as polysorbates, glucose, lactose, mannitol, sucrose, dextran, citric acid, tromethamol, triethanolamine, aminoacetic acid and/or synthetic polymers. The doxorubicin-peptide derivatives according to the invention are preferably dissolved in an isotonic buffer in a pH range of 2.0-8.0, preferably pH 5.0 to 7.0 and administered. The doxorubicin-peptide derivatives according to the invention usually have an adequate water-solubility due to the oxyethylene units in the cross-linker and/or the integration of polar amino acids into the peptide sequence such as arginine, proline, glutamine and/or glutamic acid. The solubility of the doxorubicin-peptide derivative can optionally be improved by pharmaceutical solvents such as 1,2-propane-diol, ethanol, isopropanol, glycerol and/or poly(ethylene glycol) having a molecular weight of 200 to 600 g/mol, preferably poly(ethylene glycol) having a molecular weight of 600 g/mol and/or solubility mediators such as Tween 80, cremophore or polyvinylpyrrolidone.

An important feature of the doxorubicin-peptide derivatives according to the invention is their rapid covalent binding to serum proteins via the protein-binding group which generates a macromolecular transport form of the active substance. It is known that serum proteins such as transferrin or albumin have an increased uptake into tumor tissue (Kratz F.; Beyer U. *Drug Delivery* 1998, 5, 281-299) so that they can be used within the scope of the invention as endogenous carriers for cytostatic agents. Circulating human serum albumin (HSA) which is the main protein component of human blood having an average concentration of 30 to 50 g/l (Peters T. *Adv. Protein Chem.* 1985, 37, 161-245) and which has a free cysteine group (cysteine-34 group) at the surface of the protein that is suitable for binding thiol-forming groups such as maleinimides or disulfides (WO 00/76551) is a particularly preferred serum protein. Doxorubicin-peptide derivatives can also be reacted extracorporeally with serum proteins e.g. with an amount of albumin, blood or serum intended for infusion.

In comparison to doxorubicin, protein-bound doxorubicin-peptide derivatives have a changed biodistribution and accumulate in tumor tissue due to their macromolecular character. As a result of cleavage by MMP-2 or MMP-9 in the tumor tissue, low-molecular doxorubicin-peptides are cleaved off which release doxorubicin as the active component in the tumor tissue. In experimental studies on animals protein-binding doxorubicin-peptide derivatives also surprisingly exhibited a higher efficacy than the clinical standard doxorubicin (see example 1).

BRIEF DESCRIPTION OF DRAWINGS

The invention is elucidated in more detail by the following examples in conjunction with the drawing. The following is shown in the drawing.

EXAMPLE 1

Figure 1:
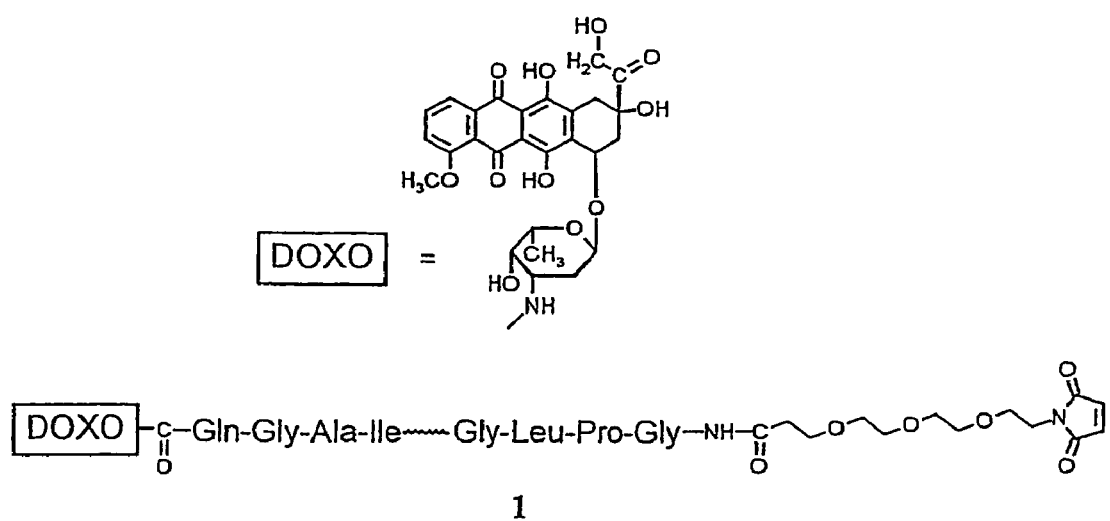
FIG. 1 shows the structural formula of the product of example 1. Gln-Gly-Ala-Ile and Gly-Leu-Pro-Gly disclosed as SEQ ID NOS 6-7, respectively.

Synthesis of 1 (see FIG. 1): 175.0 mg (0.3 mmol) doxorubicin hydrochloride, 298.5 mg (0.3 mmol) Mal-Gly-Pro-Leu-Gly-Ile-Ala-Gly-Gln (SEQ ID NO: 4) (Mal=maleinimido-triethyleneglycolic acid), 40.5 mg (0.3 mmol) 1-hydroxybenzotriazole hydrate and 98.95 μl (91.0 mg, 0.9 mmol) 4-methylmorpholine were stirred for 15 minutes at +5° C. in 50 ml anhydrous N,N-dimethylformamide (DMF). 139.36 μl (113.6 mg, 0.9 mmol) N,N'-diisopropylcarbodiimide was added and the mixture was stirred for 72 hours at +5° C. Subsequently the solvent was removed in a high vacuum, the residue was dissolved in a minimum amount of chloroform/methanol 4:1 and the product was purified by a double column chromatography on silica gel 60 (Merck, Darmstadt) using chloroform/methanol 4:1. From the fractions obtained, 1 was precipitated by adding an excess of diethyl ether and centrifuged, washed with 2×20 ml diethyl ether and again centrifuged. After drying in a high vacuum, 250 mg of 1 was obtained as a red powder. Mass (MALDI-TOF, Mr 1520.7): m/z 1543 [M+Na]$^+$, HPLC (495 nm): >98%.

Figure 2:
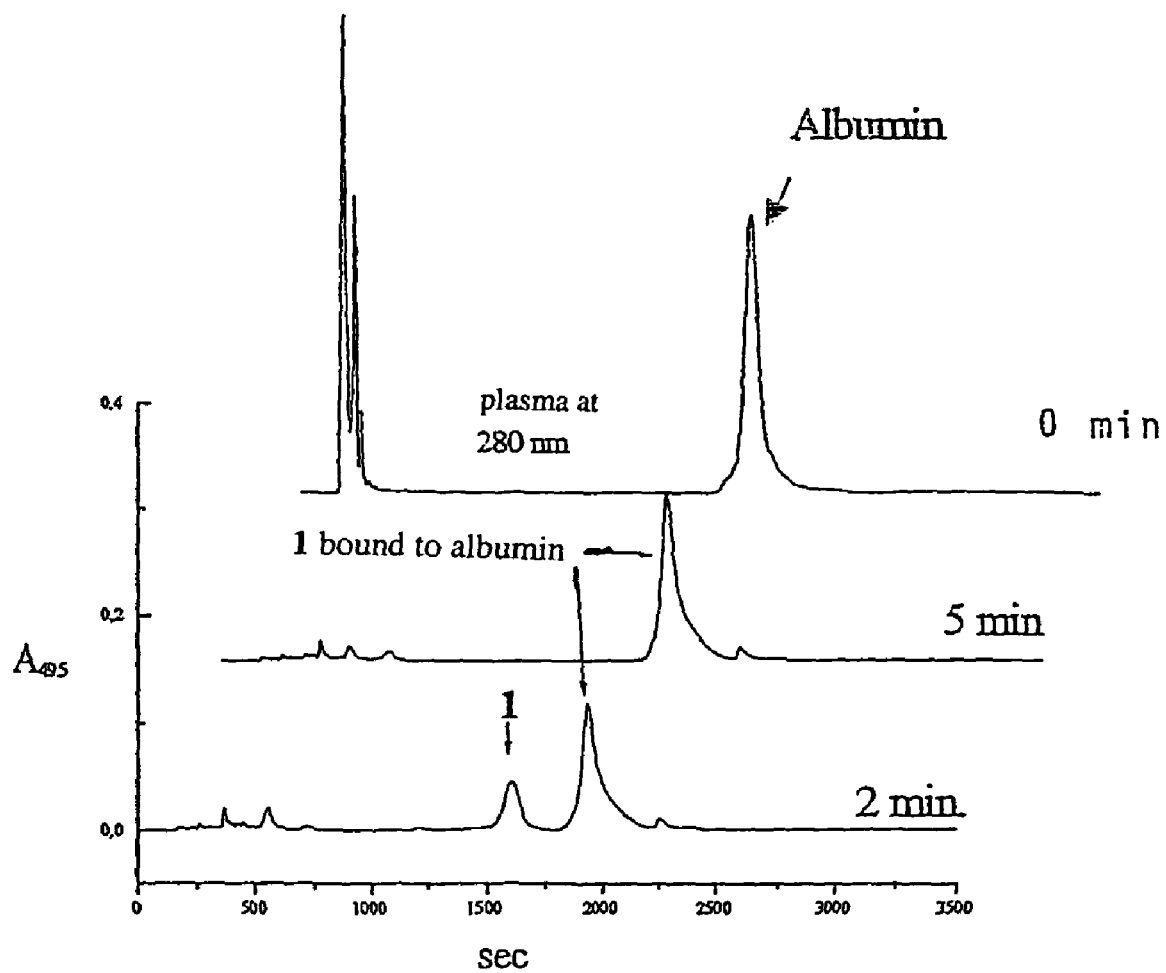
FIG. 2 shows a chromatogram of a product of incubating the compound of FIG. 1 with human plasma.

1 contains maleinimidotriethyleneglycolic acid as a water-soluble and albumin-binding component. 1 binds selectively to the cysteine-34 position of endogenous albumin in blood plasma within a few minutes (see FIG. 2).

FIG. 2 shows chromatograms of an incubation study of 1 with human plasma at 37° C. after 2 and 5 min. Concentration of 1=59 μM. HPLC: BioLogic Duo-Flow System from Biorad, Munich; Lambda 1000 Monitor from Bischoff (λ=495 nm) and Merck F-1050 fluorescence spectrophotometer (EX. 490 nm, EM. 540 nm); UV detection at 280 nm; column: Waters, 300 Å, symmetry C18 [4.6×250 mm] with precolumn; flow rate: 1.2 ml/min, mobile phase A: 27.5% CH$_3$CN, 72.5% 20 mM potassium phosphate (pH 7.0), mobile phase B: CH$_3$CN, gradient: 0-25 min 100% mobile phase A; in 25 to 40 min to 70% CH$_3$CN, 30% 20 mM potassium phosphate; 40 to 50 min 70% CH$_3$CN, 30% 20 mM potassium phosphate; 50-60 min 100% mobile phase A; injection volume: 50 μl.

The chromatograms show that a considerable proportion of 1 is already bound to albumin after 2 min incubation; after 5 min the total quantity of 1 is bound to albumin.

EXAMPLE 2

Figure 3:
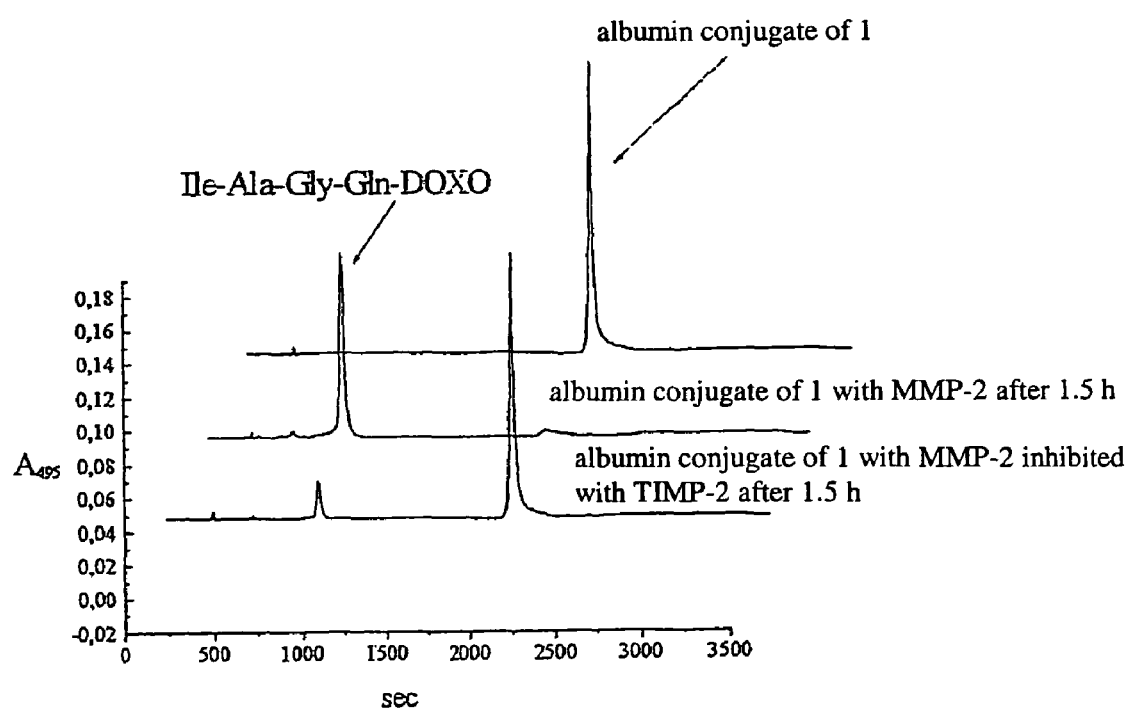

The albumin-bound form of 1 was incubated for 1.5 hours with 2 mU activated P-2 at 37° C. in the absence and presence of a two-fold excess of TIMP-2 (tissue inhibitor of MMP-2). The cleavage preparation was then subjected to a HPLC under the conditions described for FIG. 2. The concentration of anthracyclin was 100.μm. The chromatogram is shown in FIG. 3. Similar results were achieved when using MMP-9 instead of MMP-2 (MMP-2 and MMP-9 of Calbiochem FRG). The chromatogram of the preparation with MMP-2 and without TIMP-2 shows that the residue Ile-Ala-Gly-Gln-DOXO (SEQ ID NO: 5) was completely cleaved from the albumin conjugate of 1 after 1.5 hours. When MMP-2 was inhibited by TIMP-2 there was only a very slight cleavage and the albumin conjugate of 1 was almost completely preserved.

EXAMPLE 3

Figure 4:
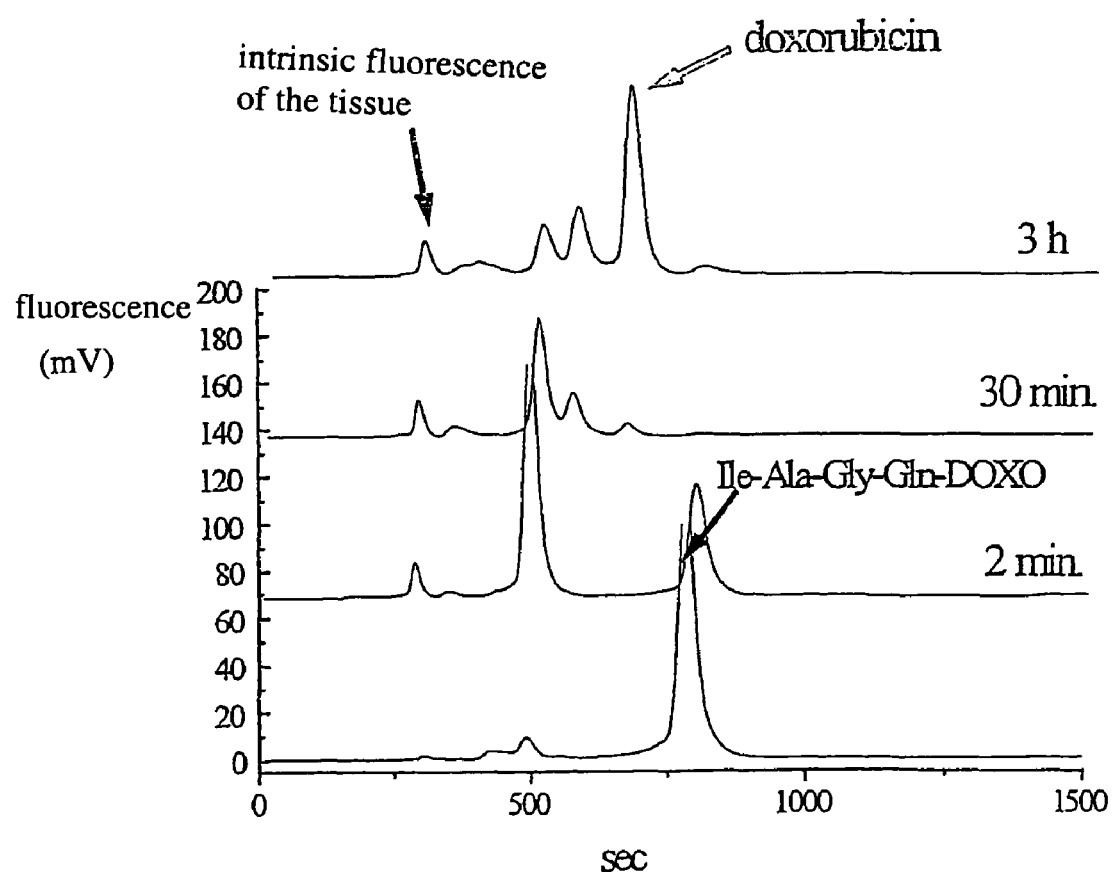

An incubation study with A375 melanoma tissue homogenate was carried out using the cleaved doxorubicin-tetrapeptide (Ile-Ala-Gly-Gln-DOXO) (SEQ ID NO: 5) obtained as described in example 2. The incubation was carried out at 37° C. The concentration of anthracyclin was 100.μm. A HPLC chromatography was carried out under the conditions of FIG. 2 after 2 min, 30 min and 3 hours. The melanoma tissue homogenate used for these experiments was prepared from A375 xenograft tumors in 50 mM Tris-HCl buffer pH 7.4 containing 1 mM monothioglycerol. FIG. 4 shows the results that were obtained.

EXAMPLE 4

Figure 5:
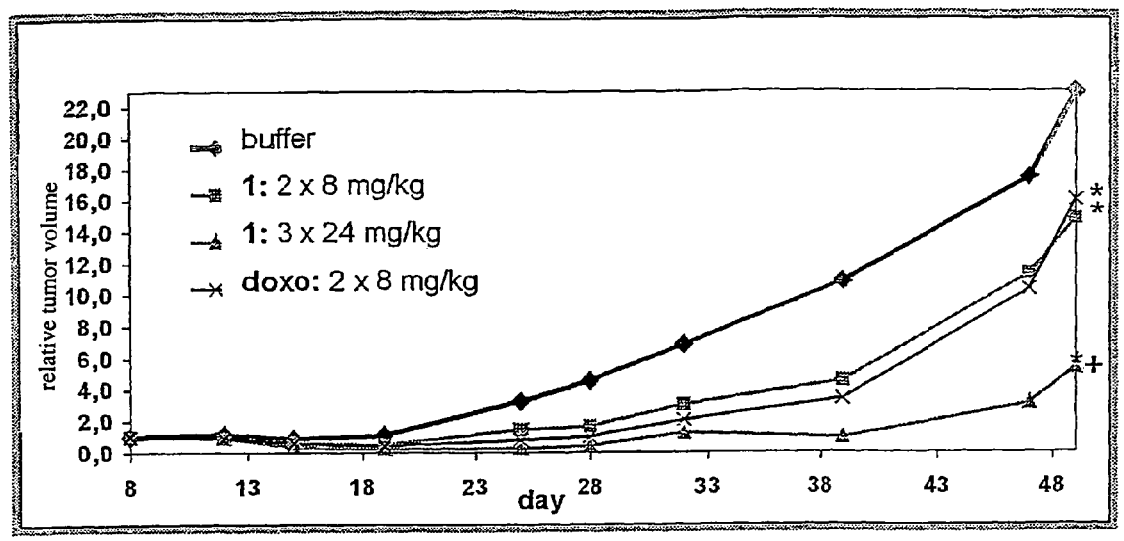
FIG. 5 shows a graphic representation of the tumor growth of an A375 melanoma with doxorubicin and the compound of FIG. 1.

The course of tumor growth of subcutaneously growing A375 melanoma xenografts that had been treated with doxorubicin and 1 [dose (i.v.); doxorubicin (=doxo): 2×13.3 μmol/kg=2×8 mg/kg doxorubicin) on days 8 and 15; 1:2×13.3 μmol/kg (=2×8 mg/kg doxorubicin equivalents) on days 8 and 15, 3×39.9 μmol/kg (=3×24 mg/kg doxorubicin equivalents) on days 8, 15 and 22 is shown in FIG. 5. The figure shows the relative tumor volume at the stated times. Animals: nacked mice; stock solution of doxorubicin (2 mg/ml); stock solution of 1:6 mg/ml in 10 mM sodium phosphate, 5% D-glucose (pH 6.4), control (buffer): glucose phosphate buffer (10 mM sodium phosphate, 5% D-glucose—pH 6.4) on days 8 and 15.

The curves in FIG. 5 very clearly show the major superiority of the doxorubicin-derivative according to the invention compared to doxorubicin. Doxorubicin results in an approximately three times larger tumor volume compared to treatment with the derivative according to the invention. This shows the surprisingly improved efficacy that is achieved with the derivative according to the invention.

---

I claim:

1. A doxorubicin-peptide of the formula I

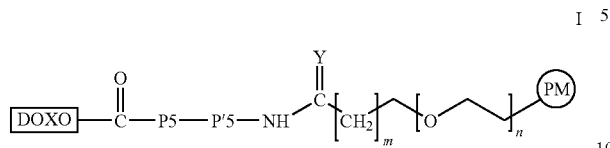

wherein
Y=O or S
n=1 to 5
m=0 to 6
$P_5$-$P'_5$ denotes a peptide sequence consisting of up to ten amino acids, said amino acids being selected from the group consisting of the twenty essential amino acids,
wherein the peptide sequence can be cleaved by the matrix metalloproteinase 2 and/or 9 (MMP-2 and/or MMP-9) and
PM is a protein-binding group which is a maleinimide group, a 2-dithiopyridyl group, a halogen acetamide group, a halogen acetate group, a disulfide group, an acrylic acid ester group, a monoalkylmaleic acid ester group, a monoalkylmaleaminic acid amide group, an isothiocyanate group or an aziridine group, which is optionally substituted and

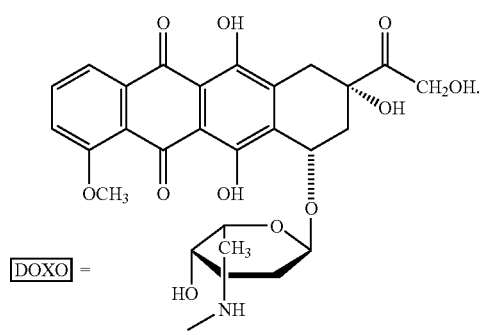

= doxorubicin is of the formula

2. A doxorubicin-peptide as claimed in claim 1, wherein PM is a maleinimide group which is optionally substituted.

3. A doxorubicin-peptide as claimed in claim 1, wherein m is <2.

4. A doxorubicin-peptide as claimed in claim 1, wherein Y=O.

5. A doxorubicin-peptide as claimed in claim 1, wherein the peptide sequence $P_5$-$P'_5$ comprises eight amino acids.

6. A doxorubicin-peptide as claimed in claim 5, wherein the peptide sequence is Gly-Pro-Gln-Gly-Ile-Ala-Gly-Gln (SEQ ID NO: 1), Gly-Pro-Leu-Gly-Ile-Ala-Gly-Gln (SEQ ID NO: 2) or Gly-Pro-Gln-Gly-Ile-Trp-Gly-Gln (SEQ ID NO: 3).

7. A doxorubicin-peptide as claimed in claim 5, wherein the peptide sequence is Gly-Pro-Leu-Gly-Ile-Ala-Gly-Gln (SEQ ID NO: 2).

8. A process for producing doxorubicin-peptide as claimed in claim 1, comprising reacting a peptide of formula III

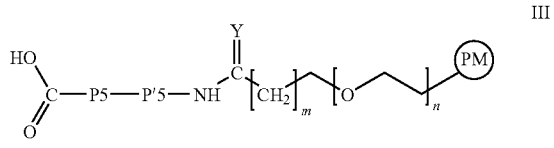

wherein
Y=O or S
n=1 to 5
m=0 to 6
$P_5$-$P'_5$ denotes a peptide sequence consisting of up to ten amino acids, said amino acids being selected from the group consisting of the twenty essential amino acids and
PM is a protein-binding group which is a maleinimide group, a 2-dithiopyridyl group, a halogen acetamide group, a halogen acetate group, a disulfide group, an acrylic acid ester group, a monoalkylmaleic acid ester group, a monoalkylmaleaminic acid amide group, an isothiocyanate group or an aziridine group, which is optionally substituted,
with doxorubicin in the presence of a carboxylic acid activation reagent.

9. The process as claimed in claim 8, wherein PM is a maleinimide group.

10. The process as claimed in claim 8, wherein the peptide derivative of formula II is obtained by reacting a peptide sequence $P_5$-$P'_5$ with a heterobifunctional cross-linker of formula II

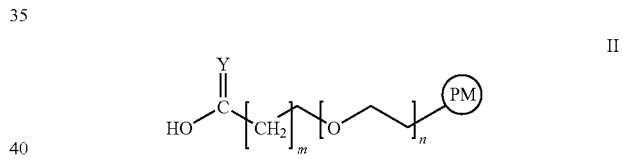

wherein
Y=O or S
n=1 to 5
m=0 to 6
PM=a protein-binding group as stated in claim 8,
in the presence of a carboxylic acid activation reagent.

11. The process as claimed in claim 8, wherein the carboxylic acid activation reagent is N,N'-dicyclohexyl-carbodiimide, N,N'-diisopropylcarbodiimide or (benzotriazol-1-yloxy)-tris (dimethylamino)phosphonium hexafluorophosphate.

12. A pharmaceutical preparation containing a doxorubicin-peptide as claimed in claim 1 as the active substance, and a pharmaceutically acceptable carrier or solvent.

13. A process for the production of a pharmaceutical preparation comprising transferring a compound according to claim 1 into a pharmaceutically acceptable solution.

14. A doxorubicin-peptide as claimed in claim 1, wherein m=1 and n=3.

15. A conjugate comprising a doxorubicin peptide of claim 1 conjugated to a carrier protein.

16. The conjugate of claim 14 wherein said carrier protein is transferrin or albumin.

17. The doxorubicin-peptide as claimed in claim 1, wherein n=2 to 5 oxyethylene units.

18. A method for inhibiting tumor growth in an animal, comprising administering to said animal an effective amount of a doxorubicin-peptide of claim 1 or a pharmaceutical composition thereof.

19. The method of claim 18, wherein said tumor is melanoma.

20. A method for treating melanoma in an animal, comprising administering to said animal an effective amount of a doxorubicin-peptide of claim 1 or a pharmaceutical composition thereof.

21. The method of claim 18, wherein said doxorubicin-peptide is administered parenterally.

22. The method of claim 18, wherein said doxorubicin-peptide is administered intravenously.

* * * * *